(12) United States Patent
Thomson et al.

(10) Patent No.: US 8,756,182 B2
(45) Date of Patent: *Jun. 17, 2014

(54) METHOD FOR QUANTIFYING AMPLITUDE OF A RESPONSE OF A BIOLOGICAL NETWORK

(75) Inventors: Ty Matthew Thomson, Arlington, MA (US); Dexter Roydon Pratt, Reading, MA (US); William M. Ladd, Cambridge, MA (US)

(73) Assignee: Selventa, Inc., Cambridge, MA (US)

( * ) Notice: Subject to any disclaimer, the term of this patent is extended or adjusted under 35 U.S.C. 154(b) by 261 days.

This patent is subject to a terminal disclaimer.

(21) Appl. No.: 13/149,022

(22) Filed: May 31, 2011

(65) Prior Publication Data

US 2012/0030162 A1 Feb. 2, 2012

Related U.S. Application Data

(60) Provisional application No. 61/350,337, filed on Jun. 1, 2010.

(51) Int. Cl.
| | | |
|---|---|---|
| *G06E 1/00* | (2006.01) | |
| *G06E 3/00* | (2006.01) | |
| *G06F 15/18* | (2006.01) | |
| *G06G 7/00* | (2006.01) | |
| *G06N 99/00* | (2010.01) | |
| *G06N 3/08* | (2006.01) | |

(52) U.S. Cl.
CPC .. *G06E 1/00* (2013.01); *G06E 3/00* (2013.01); *G06F 15/18* (2013.01); *G06G 7/00* (2013.01); *G06N 99/005* (2013.01); *G06N 3/08* (2013.01)
USPC .......................................................... 706/20

(58) Field of Classification Search
CPC ............ G06E 1/00; G06E 3/00; G06F 15/18; G06G 7/00; G06N 99/005; G06N 3/08
USPC .............................................. 706/20, 16, 15, 62
See application file for complete search history.

(56) References Cited

U.S. PATENT DOCUMENTS

| | | | | |
|---|---|---|---|---|
| 7,519,519 | B1 * | 4/2009 | Eynon et al. ...................... 703/2 |
| 2003/0096264 | A1 * | 5/2003 | Altar et al. ....................... 435/6 |
| 2004/0158407 | A1 * | 8/2004 | Ihmels et al. ................... 702/19 |
| 2005/0137805 | A1 * | 6/2005 | Lewin et al. ................... 702/19 |
| 2007/0225956 | A1 * | 9/2007 | Pratt et al. ..................... 703/11 |
| 2009/0049019 | A1 * | 2/2009 | Su et al. .......................... 707/3 |

(Continued)

OTHER PUBLICATIONS

Bolstad, "Low-level Analysis of High-density Oligonucleotide Array Data: Background, Normalization and Summarization", University of California, Berkeley Spring 2004.*

(Continued)

*Primary Examiner* — Jeffrey A Gaffin
*Assistant Examiner* — Ilya Traktovenko
(74) *Attorney, Agent, or Firm* — David H. Judson

(57) ABSTRACT

One or more measurement signatures are derived from a knowledge base of casual biological facts, where a signature is a collection of measured node entities and their expected directions of change with respect to a reference node. The knowledge base may be a directed network of experimentally-observed casual relationships among biological entities and processes, and a reference node represents a perturbation. A degree of activation of a signature is then assessed by scoring one or more "differential" data sets against the signature to compute an amplitude score. The amplitude score quantifies fold-changes of measurements in the signature. In one particular embodiment, the amplitude score is a weighted average of adjusted log-fold changes of measured node entities in the signature, wherein an adjustment applied to the log-fold changes is based on their expected direction of change. In an alternative embodiment, the amplitude score is based on quantity effects.

16 Claims, 2 Drawing Sheets

(56) References Cited

U.S. PATENT DOCUMENTS

2009/0093969 A1* 4/2009 Ladd et al. .................. 702/19
2009/0099784 A1* 4/2009 Ladd et al. .................. 702/19

OTHER PUBLICATIONS

Cui et al, "Statistical tests for differential expression in cDNA microarray experiments", Genome Biology 2003, 4:210, Published: Mar. 17, 2003.*

Kerns et al, "Application of the S-score algorithm for analysis of oligonucleotide microarrays", Science Direct, Methods 31 (2003) 274-281.*

Lakshmipathy et al, "MicroRNA Expression Pattern of Undifferentiated and Differentiated Human Embryonic Stem Cells", Stem Cells and Development, 16:1003-1016 (2007).*

* cited by examiner

METHOD FOR QUANTIFYING AMPLITUDE OF A RESPONSE OF A BIOLOGICAL NETWORK

This application claims the priority benefit of prior-filed Provisional Application Ser. No. 61/350,337, filed Jun. 1, 2010.

TECHNICAL FIELD

This disclosure relates generally to methods and techniques for characterizing the response of biological networks.

BACKGROUND OF THE RELATED ART

Acquisition of large-scale data sets representing a variety of data modalities has become a crucial aspect of the characterization of experimental systems. Such a strategy affords a broad capture of biological information in a short time and with a relative small investment of effort. Rich datasets are collected in hopes that valuable biological insights might be gained. The amount of collected information, however, can be overwhelming, making interpretation of the data difficult, and subsequent detailed biological understanding elusive.

Researchers have developed several strategies to address the management of large-scale data sets, and these strategies offer some ability to interpret the data and develop biological insight. Many of these solutions are based on measurement enrichment. For example, Gene Set Enrichment Analysis determines whether members of a gene set tend to occur toward a top (or bottom) of a list, in which case the gene set is correlated with a phenotypic class distinction. Enrichment can also be incorporated with pathway analysis where, for example, specific measurements are associated with elements of a particular biological pathway. In addition to visually connecting measurements in this way, enrichment scores can be generated using a pathway to define the set of genes. Rather than identifying the upstream pathways that lead to the data, many of these enrichment-based solutions interpret the data from a "consequence" point of view, assessing the functional impact of the changes themselves. This approach, however, requires certain assumptions about the data and its impact, such as assuming mRNA expression is directly correlated to the activity of the encoded protein. Indeed, the correlation of mRNA to encoded protein abundance is variable. Focusing on strictly consequential perspectives also fails to capture a major facet of the data that can be harnessed from an upstream "causal" perspective. Additionally, from a use perspective, the output of many of these existing data interpretation strategies is a measure of statistical enrichment, ultimately yielding a Boolean decision about pathway enrichment/activation rather than a measure of activation intensity.

Alternative strategies have been described that focus on uncovering a characteristic "signature" of measurements that results from one or more perturbations to a biological process, and subsequently scoring the presence of that signature in additional data sets as a measure of specific activity of that process. Most previous work of this type involves identifying and scoring signatures that are correlated with a disease phenotype. These phenotype-derived signatures provide significant classification power, but the lack of a mechanistic or causal relationship between a single specific perturbation and the signature means that the signature may represent multiple distinct unknown perturbations that lead to the same disease phenotype. A number of studies, however, have focused instead on measuring causal signatures based on very specific upstream perturbations either performed directly in the system of interest, or from closely-related published data. Based on the simple, yet powerful, premise that modulation of cellular pathways and the components therein are associated with distinct signatures in downstream measureable entities, causally-derived signatures enable the "cause" of the signature to be identified with high specificity from the measured "effect." These studies have demonstrated the great potential of applying a causal pathway scoring strategy to clinical problems, for example, by providing prognosis predictions in gastric cancer patients and indications of specific drug efficacy.

Given the vast potential of the information contained within large-scale data sets and the increasing ease at obtaining this data, it is desired to develop new ways of mining understanding from these data sets.

BRIEF SUMMARY

According to this disclosure, known techniques for causal pathway analysis of large data sets are extended to provide for a measure of intensity, which facilitates the comparison of biological states based on degree or amplitude of perturbation rather than comparison of likelihood of perturbation based on enrichment. The strategy is useful for the causal assessment of the activity amplitude for a broad and deep scope of biology, ranging from individual transcription factors and kinases to major signaling networks.

In one embodiment, one or more measurement signatures are derived (e.g., but without limitation, from a knowledge base of casual biological facts), where a signature is a collection of measured node entities and their expected directions of change with respect to a reference node. The knowledge base may be a directed network of experimentally-observed casual relationships among biological entities and processes, and a reference node represents a potential perturbation to a biological entity or process (i.e., an entity that is hypothetically perturbed). According to this disclosure, a "degree of activation" of a signature is then assessed by scoring one or more "differential" data sets against the signature to compute an amplitude score, sometimes referred to for convenience herein as a "network perturbation amplitude" (NPA) metric. As used herein, a "differential" data set is a data set having first and second conditions, e.g., a "treated" versus a "control" condition.

In one embodiment, the amplitude score quantifies fold changes of measurements in the signature. A fold change is a number describing how much a quantity changes going from an initial to a final value. An example of this type is an amplitude score that is a weighted average of adjusted log-fold changes of measured node entities in the signature, wherein an adjustment applied to the log-fold changes is based on their expected direction of change according to the signature. More particularly, the amplitude score is a weighted sum of log 2 fold-changes of measured node entities expected to increase in the signature minus a weighted sum of the log 2 fold-changes of measured node entities expected to decrease in the signature, divided by a total number of measured node entities in the signature.

According to a more specific embodiment, an amplitude score of this type is derived as a p-value adjusted Strength measure according to the following function:

$$\text{Strength}(f) = \frac{\sum_i (1 - pval_i)^f \times direction_i \times \log_2(FC_i)}{\sum_i (1 - pval_i)^f}$$

where $direction_i$ represents the expected direction of change according to the signature (e.g., +1, representing an increase, and −1, representing a decrease) of the $i^{th}$ measured node entity in the signature, $FC_i$ represents the measured fold-change of the $i^{th}$ measured node entity in the signature, $pval_i$ represents a p-value for $FC_j$, f is a constant, N is a number of measured node entities in the signature, and the sum over all i is the sum over all measured node entities in the signature. The constant f controls the degree to which the influence of a particular measured node entity (e.g., a measured gene) is weighted according to the significance of its fold change (e.g., as expressed by its p-value). A weight may have a unit value (i.e., "1"), or some other values, e.g., $(1-pval_i)^f$.

An alternative Strength measure with weight=1 (equivalently, f=0) is derived according to the following function:

$$\text{Strength} = \frac{\sum_i direction_i \times \log_2(FC_i)}{N}$$

As noted, the above-identified "strength"-based metrics quantify fold-changes of measurements in the signature. In the alternative, the "degree of activation" measure is one that is based on absolute changes of nodes that represent some measurable physical quantities. In this alternative embodiment, the degree of activation measure quantifies an absolute change in the nodes (corrected from the expected direction of change of each node in the signature) compared to the total quantity of the nodes. An example of this type is a Measured Abundance Signal Score (MASS), which generates an amplitude score according to the following function (with treated and control as a representative differential data set):

$$MASS = \frac{\sum_i direction_i \times (treated_i - control_i)}{\sum_i \frac{(treated_i - control_i)}{2}}$$

where $direction_i$ represents expected direction of change of an $i^{th}$ measured node entity according to the signature, $treated_i$ is a measurement for an $i^{th}$ measured node entity in a treated sample, $control_i$ is a measurement for an $i^{th}$ measured node entity in a control sample, and the sum over all i is the sum over all measured node entities in the signature.

The foregoing has outlined some of the more pertinent features of the invention. These features should be construed to be merely illustrative. Many other beneficial results can be attained by applying the disclosed invention in a different manner or by modifying the invention as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION

Figure 1:
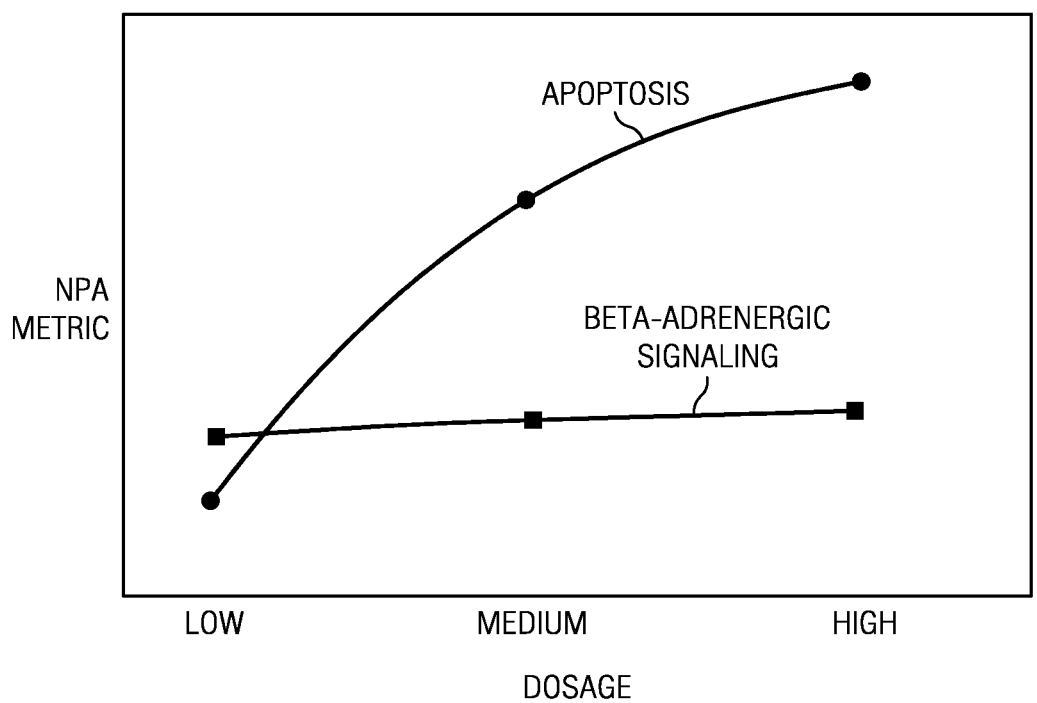
FIG. 1 illustrates a representative NPA metric graphed for two biological process networks in a dosage-series experiment.
Figure 2:
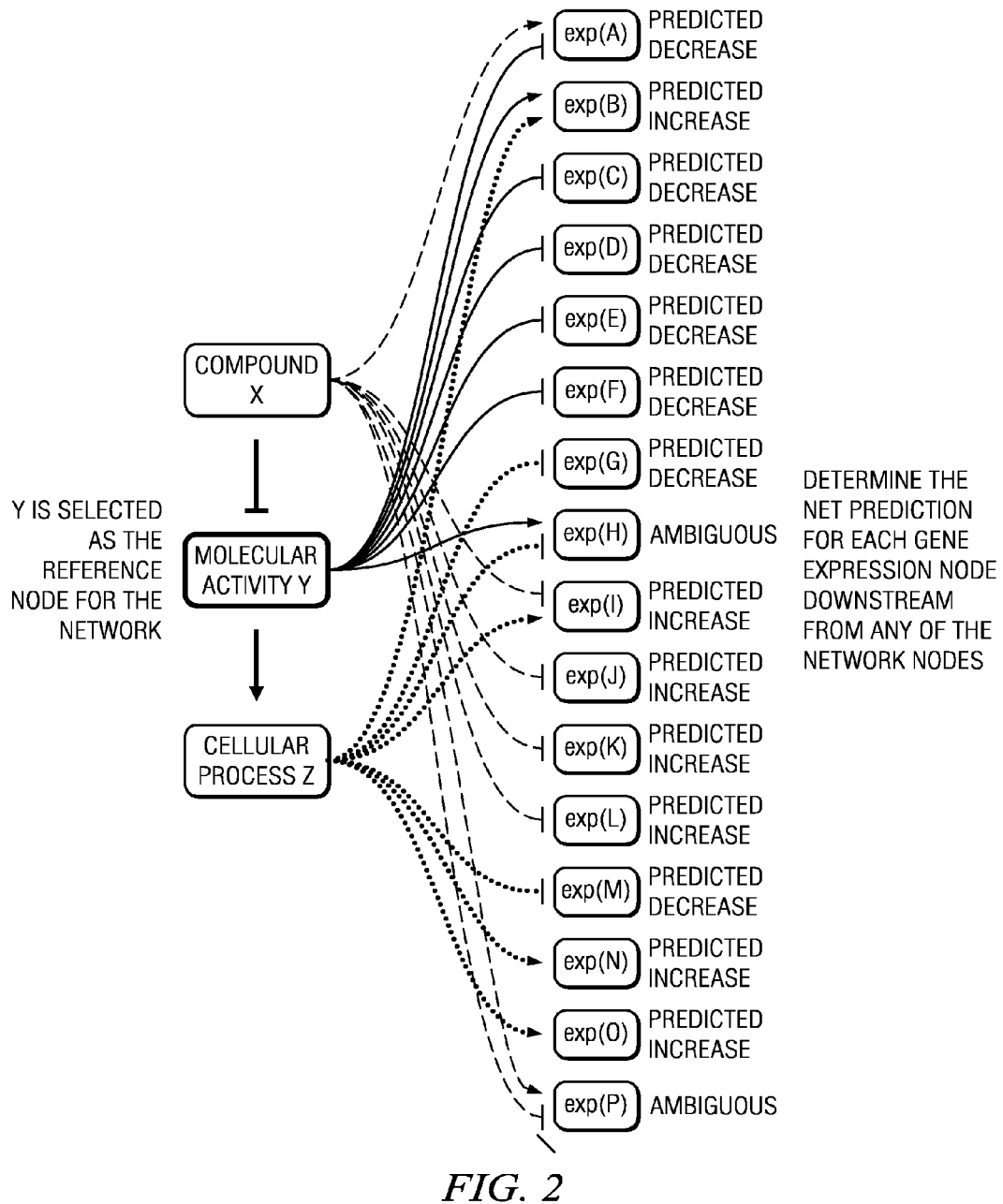
FIG. 2 illustrates how a signature can be derived from a casual network by evaluating each component of the network as a potential signature and merging the predictions of each component signature.

As described above, the techniques herein, in one embodiment, take advantage of known systems and methods for assembling and mining life science data. In particular, it is known to manage and evaluate life science data using a large-scale, specialized, literature-derived knowledgebase of causal biological facts, sometimes referred to as a Knowledge Assembly Model (KAM). A system, method and apparatus of this type are described in commonly-owned U.S. Pat. No. 7,865,534, and U.S. Publication No. 2005/0165594, the disclosures of which are incorporated herein by reference. Familiarity with these known techniques is presumed.

The techniques herein, however, are not limited to signatures derived from a casual knowledge base, as other known techniques may be used to derive the signature. Thus, in the context of one or more disclosed embodiments, the signature is "received" from a source, which source may (but is not required to) be a casual knowledge base.

As will be seen, this disclosure extends these known techniques to provide an "intensity" measure to provide for a high resolution comparison of biological states. As mentioned above, and as will be described in more detail below, there are several types of intensity measures described, namely Strength, and Measured Abundance Signal Score (MASS).

As used herein, the following terms have the following definitions:

A "knowledge base" is a directed network, preferably of experimentally-observed casual relationships among biological entities and processes;

A "node" is a measurable entity or process;

A "reference node" represents a potential perturbation to a node;

A "signature" is a collection of measurable node entities and their expected directions of change with respect to a reference node;

A "differential data set" is a data set that has data associated with a first condition, and data associated with a second condition distinct from the first condition; and A "fold change" is a number describing how much a quantity changes going from an initial to a final value, and is specifically computed by dividing the final value by the initial value.

As will be described in more detail below, one or more measurement signatures can be derived (e.g., from a knowledge base of casual biological facts), where a signature is a collection of measured node entities and their expected directions of change with respect to a reference node. Where a knowledge base is used to derive the signatures, preferably the knowledge base is a directed network of experimentally-observed casual relationships among biological entities and processes, and a reference node represents a potential perturbation. According to this disclosure, a "degree of activation" (referred to as "Strength" or "Measured Abundance Signal Score" in particular embodiments) of a signature is then assessed by scoring one or more "differential" data sets against the signature. The result of this computation is an amplitude score, measure or metric. As used herein, and as noted above, a "differential" data set is a data set having first and second conditions, e.g., a "treated" versus "control" condition, a disease versus normal condition, a disease condition versus a different disease condition, a disease treated with a first drug versus the same disease treated with a second drug, a "responder" versus a "non-responder," a patient population versus a different patient population, pre- and post-drug treatment, pre- and post-development of a disease, pre- and post-remission of a disease, and so forth. The above examples are not intended to be limiting. For purposes of explanation, several of the examples below illustrates the various degree of activation measures in the context of the treated versus control differential data set; one of ordinary skill will appreciate that the various other types of differential data described above can be substituted into the functions accordingly.

In one embodiment, a signature is defined as a set of measureable entities (for example, mRNAs) and their expected direction of change (whether they are increased or decreased) in response to a perturbation. An expected direction of change typically is a fixed value, such as +1, representing an increase, and −1, representing a decrease, although this is not a limitation. One or more scoring algorithms are then used to assess the "degree of activation" of each measurement signature. In general, the quantification approach herein (i.e., the "degree of activation" measures) validates the use of a broad, literature-derived knowledge base to score various aspects of biology that can be defined as very specific mechanisms (such as an individual protein activity) that are directly proximal to the data, or as a larger network of interest that is composed of a collection of individual mechanisms.

As a shorthand reference, but not by way of limitation, the "degree of activation" computed as described herein is sometimes referred to herein as a "network perturbation amplitude" or "NPA." As noted above, this disclosure describes several "types" of the degree of activation measure associated with a signature. The first of these types is a "strength" measure, which is a weighted average of adjusted log-fold changes of measured node entities in the signature, where the adjustment applied to the log-fold changes is based on their expected direction of change. As used herein, log refers to log 2 or log 10. Thus, the "strength" metric quantifies fold-changes of measurements in the signature.

The following is a representative example of a "strength-based" amplitude score of this type:

$$\text{Strength}(f) = \frac{\sum_i (1 - pval_i)^f \times direction_i \times \log_2(FC_i)}{\sum_i (1 - pval_i)^f}$$

In this example, $direction_i$ represents the expected direction of change according to the signature (e.g., +1, representing an increase, and −1, representing a decrease) of the $i^{th}$ measured node entity in the signature, $FC_i$ represents the measured fold-change of the $i^{th}$ measured node entity, $pval_i$ represents a p-value for $FC_i$, f is a constant that controls the degree to which the influence each fold change is weighted according to its p-value, N is a number of measured node entities in the signature, and the sum over all i is the sum over all measured node entities in the signature. This "strength at f" (or p-value adjusted strength) measure thus is the weighted geometric mean of the ratios of the measurement where the weighting factors are derived from the p-values, and the ratios are adjusted for their predicted direction of change.

For a given signature, where Strength is equal to 0, the reference node of the signature is not predicted to be differential in the experiment; where Strength>0, the reference node is predicted to be increased, and where Strength<0, the reference node is predicted to be decreased. Strength is designed with the intent that it should be comparable between experiments, assuming the experimental conditions are comparable. In other words, strength scores characterize the difference in activation between first and second biological states of a differential data set. Thus, e.g., if Strength=1.5 in a first experiment and Strength=2.0 in a second experiment, the biological entity or process corresponding to reference node of the signature is ranked as more strongly differential in the second experiment. In general, to compare any two strength scores, the control states and the general experimental system should be comparable.

An alternative "unweighted" Strength measure with weight=1 (equivalently, f=0) is derived according to the following function:

$$\text{Strength} = \frac{\sum_i direction_i \times \log_2(FC_i)}{N}$$

In particular, "unweighted" Strength is the geometric mean of the ratios of the measurements of quantities predicted by to change according to a signature, adjusted for the direction of the prediction.

Strength assumes that the ratio of change of each measurement (e.g., a measured gene) is the basis of the calculation for the metric. Thus, two measurements have the same impact on the metric if they change by the same ratio, regardless of the absolute value of their measured values. In certain circumstances, however, the impact of a change in a measured gene may be more likely to depend on the ratio of change, because the transcripts of critical genes in control systems such as transcription factors may be present in small numbers but have large effect. However, NPA metrics are meant to assess the magnitude of perturbation of the reference node of a signature, rather than the impact of changes elicited by the signature. In attempting to measure the amplitude of a process, the quantity of the effects actually observed may be more important than what those changes might cause. Thus, as an alternative to the Strength measures described above, the degree of activation measure may be based on Measured Abundance Signal Score (MASS). A MASS is an NPA based on absolute changes of nodes that represent some measurable physical quantities. In one variant, this approach is applicable to any measurement technique that quantifies a physical measurable in a manner such that measurements are proportional to absolute quantities across all measurement nodes (i.e., the measurements for different nodes can be compared directly). Thus, as one example of this latter approach, the metric is a count that represents a change in absolute node quantities in a direction supporting an increase in a process described by the signature, divided by an average of a total absolute quantity of the nodes. This approach to computing the degree of activation measure thus quantifies the absolute change in the nodes (corrected for the expected direction of change of each node in the signature) compared to the total quantity of the nodes.

The following is a representative example of Measured Abundance Signal Score generated in this manner for the treated versus control differential data set:

$$MASS = \frac{\sum_i direction_i \times (treated_i - control_i)}{\sum_i \frac{(treated_i - control_i)}{2}}$$

Here, $direction_i$ represents expected direction of change of an $i^{th}$ measured node entity according to the signature, $treated_i$ is a measurement for an $i^{th}$ measured node entity in a treated sample, and $control_i$ is a measurement for an $i^{th}$ measured node entity in a control sample, and the sum over all i is the sum over all measured node entities in the signature.

An alternative example of a metric that like MASS quantifies changes in absolute changes in abundances rather than fold changes in abundance is Total Count Score (TCS). Unlike Strength and MASS, the TCS for a signature is applied to measurements of a single biological state and produces a value characterizing that signature for those measurements. The signature is compared using a differential data set (such as treated versus control, first treatment versus second treatment, and so forth) by comparing the TCS values of the signature in each state. TCS can be computed according to the following formula:

$$TCS = \frac{\sum_i direction_i \times A_i}{\sum_j T_j}$$

where, $direction_i$ represents expected direction of change of an $i^{th}$ measured node entity according to the signature, $A_i$ is a measurement for the $i^{th}$ measured node entity in the signature, the sum over all i is the sum over all measured node entities in the signature, $T_j$ is a measurement for the $j^{th}$ measured node entity, and the sum over all j is the sum over all measured node entities regardless of whether they are in the signature. In such case, TCS for a signature is total abundance of measured entities predicted to be increased minus the total abundance of measured entities predicted to be decreased, scaled by the total abundance of all measured entities.

The following provides additional details regarding the above-described techniques.

FIG. 1 illustrates a NPA metric graphed for two biological process networks in a dosage-series experiment. As can be seen, the metric for the Apoptosis network shows a dose-dependent response, unlike the metric for the Beta-Adrenergic Signaling.

One example of a signature is a "hypothesis" derived from a knowledge base of causal biological facts. As such, a hypothesis is the linkage of a hypothetical increase in an entity or causal network of entities, a set of measurements of quantities in two compared systems, and a set of causal predictions about the polarity of state changes, where a state change is a difference in a specific measured quantity between the compared systems. The entity that is hypothetically increased is called the hypothesis root (equivalent to the reference node of a signature). In each causal prediction of the hypothesis, the hypothesis root is modeled as the cause. A hypothesis makes predictions about the direction of change for measured quantities downstream from the hypothesis root.

When considering the development of an NPA metric, specifically an NPA metric based on transcriptomic measurements, a hypothesis may be considered as a range of vectors in gene expression space. Gene expression space is used here to mean an n-dimensional space in which each dimension corresponds to the measurement of the abundance of the mRNA for one gene. The hypothesis defines a broad direction in this space, a set of vectors that have a positive value for one set of dimensions (predicted increases in mRNA abundance), a negative value for another set (predicted decreases), and may have any value for all other dimensions.

FIG. 3 provides a simple example: a three node network with Molecular Activity Y selected as the reference node makes sixteen (16) predictions, including 1) unambiguous predictions such as the decrease of exp(M), 2) ambiguous predictions such as exp(H) where one component of the network predicts an increase, while another predicts a decrease and 3) inverted predictions such as the increase of exp(J), where the inhibitory relationship between Compound X and the Molecular activity of Y requires the inversion of Compound X's predictions.

As noted, a signature may be based on a casual knowledge base, although this is not a requirement. Multiple methods exist for constructing a signature for a particular process. One alternative option is to perform a set of direct experiments in a specific biological context and construct a measurement signature from the data. Given sufficient resources, this approach is desirable because the signature can be measured from the same context in which the signature is to be applied. For example, if one is interested in how strongly a drug elicits inflammatory responses in a particular cell line, that cell line can be exposed to TNF or interleukin family ligands to derive a cell-line-specific inflammatory signature.

The techniques herein have significant advantages. Previous work has established the utility of exploring causal facets of large scale data sets, and converting this causal interpretation into a score of relative pathway activity. These demonstrations, however, are limited in scope, scoring small and general aspects of biology (for example, growth factor signaling or Ras activation). While these approaches are powerful and have demonstrated their applicability, the measurement signature scoring techniques as described herein provide even greater impact by assessing signatures across a broad swath of biological processes with high resolution, and by qualifying signature scores with appropriate statistics. Each amplitude score represents a highly abstracted view of a set of biological measurements in the context of a particular signature. As such, dozens, hundreds, or even thousands of measurements may be aggregated into a single score.

To fully understand an amplitude score and derive value from its use, additional statistics may be used to qualify the score.

There are several additional considerations when using amplitude scoring methods for scoring measurement signatures. Preferably, scores are meant to be directly compared between different treatment/control contrasts only when using the same signature. Scores cannot be quantitatively compared between two different signatures because signatures are a surrogate for the reference node (a biological entity or process) that is being scored, and thus the relationship between the fold-changes (or magnitudes) of the measurables in the signature and the degree of activation of the reference node may differ from one reference node to another. For example, a ten-fold change in the amount of active transcription factor may result in different fold-changes in gene expression, depending on the transcription factor. One transcription factor may regulate the expression of genes that are already highly expressed and thus may only exhibit a two-fold change in average expression, while another transcription factor may regulate genes that are normally not expressed, and thus may exhibit a 100-fold-change in average expression. The pattern of scores across a series of differential data sets (e.g., multiple treated/control pairs), however, can be qualitatively compared between two different signatures. Likewise, magnitude of scores cannot be directly compared between two amplitude scoring methods, but the pattern of scores across scoring methods can be compared qualitatively, keeping in mind that the scoring methods may be assessing different aspects of the data.

The NPA scoring approach is useful in a clinical setting where (for example) the activity of a particular protein may be difficult to measure directly, while its activity can be robustly inferred from a signature of causally-related downstream measurables that can be more-readily measured. NPA scoring introduces several significant advances over previous work.

The techniques described herein are implemented using computer-implemented enabling technologies such as described in commonly-owned, co-pending applications U.S. Publication No. 2005/00038608, No. 2005/0165594, No. 2005/0154535, and No. 2007/0225956. These patent applications, the disclosures of which are incorporated herein by reference, describe a casual-based systems biology modeling tool and methodology. In general, this approach provides a software-implemented method for hypothesizing a biological relationship in a biological system that uses a database comprising a multiplicity of nodes representative of biological elements, and relationship descriptors describing relationships between nodes, the nodes and relationship descriptors in the database comprising a collection of biological assertions from which one or more candidate biological assertions are chosen. After selecting a target node in the database for investigation, a perturbation is specified for the target node. In response, given nodes and relationship descriptors of the database that potentially affect or are affected by the target node are traversed. In response to data generated during the traversing step, candidate biological assertions can be identified for further analysis.

Aspects of this disclosure (such as the calculation of the Strength, MASS and TCS metrics) may be practiced, typically in software, on one or more machines. Generalizing, a machine typically comprises commodity hardware and software, storage (e.g., disks, disk arrays, and the like) and memory (RAM, ROM, and the like). The particular machines used in the system are not a limitation of the present invention. A given machine includes network interfaces and software to connect the machine to a network in the usual manner. The subject matter may be implemented as a standalone product, or as a managed service using a set of machines, which are connected or connectable to one or more networks. More generally, the product or service is provided using a set of one or more computing-related entities (systems, machines, processes, programs, libraries, functions, or the like) that together facilitate or provide the inventive functionality described above. In a typical implementation, the service comprises a set of one or more computers. A representative machine is a network-based server running commodity (e.g. Pentium-class) hardware, an operating system (e.g., Linux, Windows, OS-X, or the like), an application runtime environment (e.g., Java, .ASP), and a set of applications or processes (e.g., AJAX technologies, Java applets or servlets, linkable libraries, native code, or the like, depending on platform), that provide the functionality of a given system or subsystem. A display may be used to provide an output of the Strength, MASS or TCS metric. As described, the product or service may be implemented in a standalone server, or across a distributed set of machines. Typically, a server connects to the publicly-routable Internet, an intranet, a private network, or any combination thereof, depending on the desired implementation environment.

Having described our invention, what we now claim is as follows.

The invention claimed is:

1. A non-transitory computer-readable storage medium storing a computer readable program of computer instructions, wherein the computer readable program when executed on a computer causes the computer to carry out the following operations:
   receiving a signature that is a collection of measurable node entities and their expected directions of change with respect to a reference node; and
   assessing a degree of activation of the signature by scoring one or more data sets against the signature to compute an amplitude score;
   wherein the amplitude score is a sum of adjusted log-fold changes of measured node entities in the signature divided by a number of node entities in the signature, where an adjustment applied to the log-fold changes is made by (i) multiplying by −1 the log-fold changes of those measured node entities expected a priori to decrease in response to an increase in the reference node, and (ii) multiplying by +1 the log-fold changes of those measured node entities expected a priori to increase in response to an increase in the reference node.

2. The computer-readable storage medium as described in claim 1 where the amplitude score is computed from a differential data set.

3. The computer-readable storage medium as described in claim 2 wherein the differential data set is a data set that has two conditions, a first condition, and a second condition.

4. The computer-readable storage medium as described in claim 3 wherein the first condition and the second condition are one of: a treated condition and a control condition, a disease condition and a non-diseased condition, a first disease condition and a second disease condition, a first patient population and a second patient population, a treatment with a first drug and the treatment with a second drug, a responder and a non-responder, pre- and post-drug treatment, pre- and post-development of a disease, and pre- and post-remission of a disease.

5. The computer-readable storage medium as described in claim 1, where an adjustment applied to the log-fold changes further includes multiplying the log fold-changes by a weighting factor.

6. The computer-readable storage medium as described in claim 1 wherein the amplitude score is a sum of log 2 fold-changes of measured node entities expected to increase in the signature minus the sum of the log 2 fold-changes of measured node entities expected to decrease in the signature, divided by a total number of measured node entities in the signature.

7. The computer-readable storage medium as described in claim 2 wherein the amplitude score quantifies a change in absolute node quantities in an expected direction of change supporting a directional change in a process described by the signature, divided by a measure of total absolute quantity of the nodes.

8. The computer-readable storage medium as described in claim 7 wherein the change in absolute node quantities is corrected for a direction of change of each node in the signature.

9. The computer-readable storage medium as described in claim 1 wherein the signature is derived from a knowledge base, wherein the knowledge base is a directed network of causal relationships among biological entities and processes.

10. An article comprising a non-transitory tangible machine-readable medium that stores a program, the program being executable by a machine to perform a method comprising:
   receiving a signature derived from a knowledge base of casual biological facts, where the signature is a collection of measured node entities and their expected directions of change with respect to a reference node; and
   scoring one or more data sets against the signature to compute an amplitude score, wherein the amplitude score is a sum of adjusted log-fold changes of measured node entities in the signature divided by a number of node entities in the signature, where an adjustment applied to the log-fold changes is made by (i) multiplying by a negative value the log-fold changes of those measured node entities expected, based on a prior observation independent of the data set being evaluated, to decrease in response to an increase in the reference node, and (ii) multiplying by a positive value the log-fold changes of those measured node entities expected, based on a prior observation independent of the data set being evaluated, to increase in response to an increase in the reference node.

11. The article as described in claim 10 wherein the amplitude score is generated according to the following function:

$$\text{Strength} = \frac{\sum_i direction_i \times \log_2(FC_i)}{N}$$

where $direction_i$ and $FC_i$ represent expected direction of change and measured fold-change of an $i^{th}$ measured node entity, and N is a number of measured node entities in the signature.

12. The article as described in claim 10 wherein the amplitude score is generated according to the following function:

$$\text{Strength}(f) = \frac{\sum_i (1 - pval_i)^f \times direction_i \times \log_2(FC_i)}{\sum_i (1 - pval_i)^f}$$

wherein $pval_i$ is a p-value for FCi, and f is a constant that controls the degree to which the influence each fold change is weighted according to its p-value.

13. The article as described in claim 10 wherein the knowledge base is a directed network of experimentally-observed causal relationships among biological entities and processes.

14. The article as described in claim 10 wherein the reference node represents a potential perturbation to a biological entity or process.

15. The article as described in claim 10 wherein an adjustment to the log fold changes further includes multiplying the log fold-changes by a weighting factor.

16. An article comprising a non-transitory tangible machine-readable medium that stores a program, the program being executable by a machine to perform a method comprising:

receiving a signature derived from a knowledge base of casual biological facts, where the signature is a collection of measured node entities and their expected directions of change with respect to a reference node; and scoring one or more data sets against the signature to compute an amplitude score according to the following function:

$$MASS = \frac{\sum_i direction_i \times (treated_i - control_i)}{\sum_i \frac{(treated_i - control_i)}{2}}$$

where $direction_i$ represents expected direction of change of an $i^{th}$ measured node entity, $treated_i$ is a measurement for an $i^{th}$ measured node entity in a treated sample, and $control_i$ is a measurement for an $i^{th}$ measured node entity in a control sample.

* * * * *